United States Patent [19]

Yasuhara et al.

[11] 4,212,990

[45] Jul. 15, 1980

[54] METHOD FOR PRODUCING CYCLOHEXANE DERIVATIVES DIRECTLY FROM AROMATIC HYDROCARBONS

[75] Inventors: Yutaka Yasuhara; Masaki Nishino; Seikichi Matsuhira, all of Nagoya, Japan

[73] Assignee: Toray Industries, Inc., Tokyo, Japan

[21] Appl. No.: 822,140

[22] Filed: Aug. 5, 1977

Related U.S. Application Data

[63] Continuation-in-part of Ser. No. 581,788, May 29, 1975, Pat. No. 4,067,915.

[51] Int. Cl.$^2$ .................. C07C 29/00; C07C 35/08; C07C 67/04; C07C 69/14
[52] U.S. Cl. .................. 560/241; 568/832; 568/834; 568/835; 585/269; 568/376
[58] Field of Search .................. 560/241; 260/617; 568/832, 834, 835

[56] References Cited

U.S. PATENT DOCUMENTS

| | | | |
|---|---|---|---|
| 3,493,605 | 2/1970 | Selwitz | 560/241 |
| 3,547,982 | 12/1970 | McKeon et al. | 560/241 |

FOREIGN PATENT DOCUMENTS 47-20129  9/1972  Japan .................. 560/241

Primary Examiner—Vivian Garner
Attorney, Agent, or Firm—Miller & Prestia

[57] ABSTRACT

Cyclohexane derivatives such as cyclohexanol, and cyclohexyl carboxylates are produced directly from aromatic hydrocarbons. The reaction may be carried out, under hydrogenation conditions, by reacting an aromatic hydrocarbon with hydrogen and a reagent selected from the group consisting of water and carboxylic acids in the presence of a strong acid and a hydrogenation catalyst.

17 Claims, No Drawings

METHOD FOR PRODUCING CYCLOHEXANE DERIVATIVES DIRECTLY FROM AROMATIC HYDROCARBONS

RELATED APPLICATION

This application is a continuation-in-part of U.S. Application Ser. No. 581,788 filed May 29, 1975, now U.S. Pat. No. 4,067,915. While the aforementioned application is directed to the production of the halogeno compounds disclosed herein, this application is directed to the production of the hydroxy and acyloxy derivatives, and particularly emphasizes the practice of such a process with a catalyst comprising a combination of at least two noble metals.

This invention relates to a method for producing cyclohexane derivatives. More specifically this invention relates to a method for producing cyclohexane derivatives represented by following Formula (I) directly from an aromatic hydrocarbon:

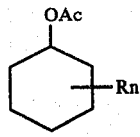

(I)

wherein Ac is hydrogen or an acyl group having 1 to 3 carbon atoms, R is a lower alkyl group having 1 to 3 carbon atoms and n is an integer from 0 to 2.

The cyclohexanol derivatives are very important raw materials in synthetic chemical industries. Cyclohexanol and its ester derivatives are used as raw materials for making synthetic polymers or solvents.

Heretofore, various methods for producing cyclohexanol derivatives have been proposed. Cyclohexanol, for example, can be produced by oxidation of cyclohexane with molecular oxygen in the presence of boric acid or a transition metal catalyst such as cobalt naphthenate. Cyclohexanol can also be obtained by hydrogenation of phenol which can be produced by oxidation of cumene prepared from benzene. All of these methods used for commercial production of cyclohexanol have hydrogenation and oxidation steps. So far as the hydrogenation process step is concerned, the conversion of the starting materials and the selectivity of the products are substantially quantitative. But the oxidation process for introducing a hydroxyl group onto the benzene nucleus or into the cyclohexane ring is only barely satisfactory, because the process often includes complex operations or the percentage conversion in the process should be kept comparatively low in order to obtain products with a high selectivity.

The cyclohexanol derivatives of Formula (I) can be produced from cyclohexene in comparatively good yield. Therefore, if cyclohexene can be obtained from benzene by selective hydrogenation, this route from benzene to the cyclohexanol derivatives is expected to be a good method for producing the cyclohexanol derivatives. Thus some methods of selective hydrogenation of benzene to cyclohexene have been proposed in U.S. Pat. Nos. 3,391,206 and 3,793,383 etc. and in German Application 2,221,137.

In these known methods, however, the conversion of benzene should usually be kept at an extremely low level to obtain a high selectivity of cyclohexene, because cyclohexene is hydrogenated more easily than benzene. In some cases a catalyst of complex composition must be used in the selective hydrogenation. Therefore, the industrial application of the method is very difficult.

Thus, the object of the present invention is to provide a method for producing cyclohexanol derivatives represented by Formula (I) directly from benzene and its derivatives in one step.

We have now found that the cyclohexanol derivatives having the general Formula (I) can be obtained by allowing the aromatic hydrocarbon to react with a compound HOAc, wherein Ac is the same as mentioned above, under hydrogenation conditions in the presence of a strong acid and a hydrogenation catalyst.

The type of aromatic hydrocarbon used as a starting material is not essentially restricted, but from the practical point of view benzene derivatives having a few alkyl substituents having a carbon number of 1 to 3, are preferable. For example, benzene, toluene, ethylbenzene, cumene and xylenes are preferably used. Benzene is most preferable. The quality of the aromatic hydrocarbon is also not specifically restricted, so far as it does not contain impurities which cause activity of the hydrogenation catalyst to deteriorate. An aromatic hydrocarbon which may be fed to a conventional hydrogenation process is preferably used in the present invention.

The amount of the aromatic hydrocarbon may be 0.1 to 40 mol%, preferably 2.0 to 40 mol%, on the basis of the total amount of the aromatic hydrocarbon and the reagent HOAc.

The reagent HOAc is water or a carboxylic acid. The carboxylic acids having 1 to 3 carbon atoms such as formic, acetic and propionic acids are preferably used. Acetic acid is most preferable among the carboxylic acids.

The strong acid used in the present invention may be a protonic acid having an acidic dissociation constant pKa of less than 4.0, preferably 3.0, more preferably 2.0, or a Lewis acid having an acid-acting property comparable thereto and having stability under reaction conditions in the present invention. The strong acid may be sulfuric acid, hydrogen chloride, hydrogen bromide, hydrogen iodide, phosphoric acid, or acidic sulfate such as potassium bisulfate, ammonium bisulfate, trifluoroacetic acid, trifluoromethanesulfonic acid, an alkanesulfonic acid, such as methanesulfonic acid, cation exchange resin, boron trifluoride, a heteropolyacid such as phosphotungstic acid, silicotungstic acid, phosphomolybdic acid, or silicomolybdic acid, an aromatic sulfonic acid such as benzenesulfonic acid, toluenesulfonic acid, or a solid acid such as alumina, silica alumina, crystalline aluminosilicate, titania or a mixture thereof, etc.

The presence of the strong acid in the reaction mixture is essential to the invention. The amount of the strong acid may preferably be more than 0.01 mol% on the basis of the reagent HOAc which exists in the reaction mixture. A still more preferable amount is more than 2 mol%.

Some quantities of cyclohexyl ester of a strong acid may be produced when the strong acid utilized is an oxyacid. For practical purposes, such an ester may be hydrolyzed to cyclohexanol or its derivative.

In the present invention the conversion of the aromatic hydrocarbon may preferably be less than 80%. At the conversion of more than 80%, the selectivity of the cyclohexane derivative (I) becomes comparatively low.

The hydrogenation catalyst used in the present invention may usually contain Group VIII metals or its compounds. The Group VIII metals may preferably be noble metals selected from the group consisting of ruthenium, rhodium, palladium, iridium and platinum. Ruthenium, rhodium, and palladium are more preferable. The catalyst may contain at least one noble metal. The combined use of two or more metals may be effective, and may fall within the range of this invention. In some cases it is advantageous to use a catalyst comprising two or more noble metals in combination, such as ruthenium-rhodium, rhodium-palladium, palladium-osmium, or rhodium-ruthenium-platinum. Such a catalyst may be more effective than a catalyst comprising a single noble metal.

The hydrogenation catalyst may further contain, as a subcomponent, at least one metal selected from the group consisting of silver, copper, gold and rhenium. These metals may be alloyed with the noble metal or metals. The usual hydrogenation catalysts for aromatic hydrocarbons may be used in the present invention.

The hydrogenation catalyst may be used in optional forms, such as sponge, fine powder, colloid, and supported form. For example, active carbon, alumina, silica, silica-alumina, boria, titanic oxide, niobium pentoxide, tantalum pentoxide, tungsten trioxide, molybdenum oxide, zeolites, asbestos, other known solid acids and cation exchange resins may be used as carrier. Some acidic carriers may play a role as the strong acid.

The quality of hydrogen gas used in the present invention is not specifically restricted except that the hydrogen may not contain impurities deteriorating the activity of the hydrogenation catalyst. Hydrogen may contain an inert gas such as nitrogen, helium, argon, carbon dioxide or methane.

The pressure of hydrogen does not essentially influence the reaction of the present invention. The preferable partial pressure of hydrogen is 0.01 to 300 kg/cm$^2$, preferably 0.5 to 150 Kg/cm$^2$. In view of the reaction rate and the pressure restriction of the reaction apparatus, the reaction may preferably be carried out under a pressure of 0.01–500 Kg/cm$^2$, more preferably 0.5–150 Kg/cm$^2$. The reaction temperature is 0°–300° C., preferably 20°–200° C.

In the embodiments of the present invention, the reaction may be carried out in an inert solvent such as methanol, dioxane, cyclohexane or n-octane, etc.

The reaction products of the present invention are mainly cyclohexanol derivatives of Formula (I) and cyclohexane or its alkyl derivatives. In some cases, cyclohexane, phenyl cyclohexane, cyclohexanone, methylcyclopentane or their alkyl derivatives are produced. The amounts of other by-products are negligible under usual reaction conditions. The recovery of the cyclohexanol derivatives (I) from the reaction mixture can be easily carried out according to conventional methods. The reaction of the present invention may be carried out either continuously or batchwise.

The mechanisms of the reaction in this invention have not been clearly understood, but the practical superiority of the present invention may be explained as follows in comparison with the selective hydrogenation of benzene to cyclohexene mentioned above. In the latter reaction, it is very difficult to enhance the conversion of benzene without sacrificing the selectivity of cyclohexene, because cyclohexene is more easily hydrogenated than benzene. On the other hand, in the former reaction which may be referred to as a "hydrogenohydration" process, the products of the Formula (I) result from the addition of the reagent HOAc such as water, etc. to an intermediate carbonium ion formed by the protonation of the intermediate cycloolefins which are formed in the hydrogenation step. The products may usually be less reducible than benzene, therefore, it is possible to enhance the conversion of benzene to obtain final products of the Formula (I) with minimum sacrifice of selectivity.

The following Examples will serve to further illustrate the present invention. The terms, conversion, yield and selectivity, used in the Examples are defined as follows:

conversion (%) =
$$\frac{\text{(amount of reacted aromatic hydrocarbon)}}{\text{(amount of aromatic hydrocarbon charged)}} \times 100$$

yield (%) =
$$\frac{\text{(amount of a product (mols))}}{\text{(amount of aromatic hydrocarbon charged (mols))}} \times 100$$

selectivity (%) =
$$\frac{\text{(amount of a product (mols))}}{\text{(amount of reacted aromatic hydrocarbon (mols))}} \times 100$$

EXAMPLE 1

In a 100 ml. flask were placed 10 ml. of glacial acetic acid, 4 ml. of benzene, 1 ml. of boron trifluoride-diacetic acid complex, and 0.5 g. of 5% of ruthenium-on-carbon catalyst. Stirring was provided by a bar magnet (sheathed with poly-tetrafluoroethylene) placed inside the flask. The bar magnet was set in motion by an external magnetic stirrer. After the flask was flushed with hydrogen, the contents of the flask were warmed to 70° C. for 10 hours under atmospheric pressure of hydrogen. Then, the flask was chilled in an ice-water bath, and into the flask 60 ml. of ether was added. The ether layer, separated, was washed with 10% sodium carbonate solution and with saturated sodium chloride solution and was subjected to analysis by means of a gas-liquid chromatograph. This analysis showed the conversion of the benzene was 1.2%, and the selectivity of cyclohexyl acetate was 1%.

EXAMPLES 2–4

Hydrogenation catalysts were examined for activity and selectivity in conversion of benzene to cyclohexyl acetate. In each experiment, an appointed volume of glacial acetic acid, an appointed volume of benzene, 1 ml. of boron trifluoride-diacetic acid complex and an appointed amount of a hydrogenation catalyst were treated with atmospheric pressure of hydrogen in a manner similar to that set forth in Example 1. The following Table shows the reaction conditions and the results obtained.

TABLE 1

| Example No. | Acetic Acid (ml) | Reaction conditions | | | | Products | |
| | | Benzene (ml) | Catalyst (mg) | Temp. (°C.) | Time (hr.) | Yield of Cyclohexane (%) | Selectivity of Cyclohexl acetate (%) |
| --- | --- | --- | --- | --- | --- | --- | --- |
| 2 | 13 | 5 | 5% Ru/C 200 | 75 | 12 | 0.8 | 5 |

TABLE 1-continued

| Example No. | Acetic Acid (ml) | Reaction conditions Benzene (ml) | Catalyst (mg) | Temp. (°C.) | Time (hr.) | Products Yield of Cyclohex- ane (%) | Selectivity of Cyclohexl acetate (%) |
|---|---|---|---|---|---|---|---|
| 3 | 10 | 4 | 9% Pd/C 500 | 70 | 6 | 4 | 1 |
| 4 | 10 | 4 | PtO$_2$ 200 | 70 | 6 | 12 | 0.6 |

EXAMPLE 5

In a manner similar to that set forth in Example 1, 5 ml. of benzene, 13 ml. of 50% sulfuric acid, and 0.5 g. of 5% ruthenium-on-carbon catalyst, were treated with atmospheric pressure of hydrogen, at 70° C. for 12 hours. The analysis of the reaction mixture, by means of a gas-liquid chromatograph, showed that the conversion of the benzene was 1.1%, and the selectivity of cyclohexanol was 1.8%.

EXAMPLE 6

In a high pressure glass bomb with a bar magnet (sheathed with polytetrafluoroethylene) set in motion by an external magnetic stirrer, were placed 10 ml. of glacial acetic acid, 4 g. of benzene, 1 ml. of boron trifluoride-diacetic acid complex, and 0.2 g. of 5% ruthenium-on-carbon catalyst. Stirring was provided by a bar magnet (sheathed with polytetrafluoroethylene) placed in advance inside the bomb. The contents of the bomb were heated at 75° C., pressured with 5 Kg/cm$^2$G of hydrogen, and stirred for one hour. Then, the bomb was chilled in an ice-water bath. The reaction mixture was treated in a manner similar to that set forth in Example 1, and subjected to analysis using a gas-liquid chromatograph. This analysis showed that the conversion of the benzene was 5.2%, and the selectivity of cyclohexyl acetate was 3.4%.

EXAMPLES 7-24

In each experiment, 1 ml. of acetic acid, 1 g. of benzene, 0.5 ml. of boron trifluoride-diacetic acid complex, and 50 mg. of a hydrogenation catalyst were treated with 5 Kg/cm$^2$G of hydrogen at 70° C. in a manner similar to that set forth in Example 6. The following Table shows the results obtained.

TABLE II

| Example No. | Catalyst | Time (hr.) | Yield of Cyclohexane (%) | Selectivity of Cyclohexyl acetate (%) |
|---|---|---|---|---|
| 7 | 1% Pd/C | 20 | 3.1 | 0.6 |
| 8 | 2% Pd/SiO$_2$ | 20 | 8.4 | 0.7 |
| 9 | 2% Pd/Al$_2$O$_3$ | 20 | 2.8 | 3.2 |
| 10 | 2% Pd/WO$_3$ | 20 | 1.0 | 2.0 |
| 11 | 2% Rh/SiO$_2$ | 3.3 | 17.3 | 0.5 |
| 12 | 2% Rh/Zeolite | 4.1 | 9.4 | 0.5 |
| 13 | 2% Rh/WO$_3$ | 3.6 | 18.0 | 0.5 |
| 14 | 2% Rh/Al$_2$O$_3$ | 2.3 | 20.3 | 0.7 |
| 15 | 2% Rh/C | 6.5 | 17.0 | 0.9 |
| 16 | 2% Ru/SiO$_2$ | 20 | 0.9 | 16.7 |
| 17 | 2% Ru/Al$_2$O$_3$ | 20 | 0.3 | 18.5 |
| 18 | 2% Ru/Zeolite | 20 | 0.2 | 7.2 |
| 19 | 2% Ru/WO$_3$ | 18.3 | 11.3 | 4.7 |
| 20 | 2% Pt/C | 6 | 13.1 | 0.6 |
| 21 | 2% Pt/SiO$_2$ | 0.5 | 21.7 | 0.1 |
| 22 | 2% Pt/WO$_3$ | 5 | 17.6 | 0.5 |
| 23 | 2% Ir/C | 3.5 | 9.8 | 0.2 |
| 24 | 2% Ir/Al$_2$O$_3$ | 1.8 | 17.6 | 0.1 |

EXAMPLE 25

In a manner similar to that set forth in Example 6, 4 g. of benzene, 8 ml. of 55% sulfuric acid, and 0.2 g. of 5% ruthenium-on-carbon catalyst were treated. After a reaction time of 4.5 hours the reaction mixture was analyzed by means of a gas-liquid chromatograph. The data showed that the conversion of the benzene was 6%, and the selectivity of cyclohexanol was 1.5%.

EXAMPLE 26

A palladium-containing cation exchange resin was prepared from 3.5 g. of tetraamine palladium (II) dichloride; Pd(NH$_3$)$_4$Cl$_2$, 30 g. of Amberlyst 15 (a cation exchange resin supplied from Rohm & Haas Co.) in the sodium form. They were mixed in 300 ml. of distilled water, stirred for 90 min., and filtered. The solid was washed with distilled water, then with ethanol, and dried at 100° C. under reduced pressure. The resin was treated with 300 ml. water and 80 ml. of an 80% aqueous solution of hydrazine at 80° C. for 40 min., and filtered, and then washed with water. The resin was placed on a column and eluted with 5% hydrochloric acid, and washed with about 2,000 ml. water (at that point it was chloride free), then with alcohol and finally with ether. It was dried at 100° C. for 2 hours under reduced pressure. The product was a catalyst comprising an ion exchange resin of sulfonic acid type having zero valent palladium in its resin matrix.

The catalyst was used for the hydrogenohydration of benzene. In a manner similar to that set forth in Example 6, 3 ml. of glacial acetic acid, 2 g. of benzene, and 0.2 g. of the said catalyst were heated at 110° C. for 20 hours under a hydrogen pressure of 5 Kg/cm$^2$G. The analysis of the reaction mixture by means of a gas-liquid chromatograph showed that the conversion of the benzene was 4.6%, and the selectivity of cyclohexyl acetate was 0.3%.

EXAMPLES 27-31

In a manner similar to that set forth in Example 26, the preparation of catalysts and the hydrogenohydration of benzene were carried out. In each case, 3 ml. of glacial acetic acid, 2 g. of benzene, and 0.2 g. of a catalyst were treated under 5 Kg/cm$^2$G of hydrogen at an appointed temperature for an appointed reaction time. The following Table shows the results obtained.

TABLE III

| Example No. | Catalyst | Temp. (°C.) | Time (hr.) | Yield of Cyclo- hexane (%) | Selectivity of Cyclohexyl acetate (%) |
|---|---|---|---|---|---|
| 27 | Pd/Amberlyst 15 | 95 | 15 | 4.7 | 0.1 |
| 28 | Pd/Amberlite 200 | 95 | 15 | 1.1 | 0.2 |
| 29 | Rh/Amberlyst 15 | 75 | 4 | 7.2 | 0.3 |
| 30 | Rh/Amberlite 200 | 75 | 4 | 17.2 | 0.1 |
| 31 | Ru/Amberlite 200 | 75 | 30 | 5.8 | 1.5 |

In Table III, the following notes are applicable:

In Example 27, the same catalyst as that of Example 8 was used.

In Example 28, the catalyst was prepared by using 0.7 g. of $Pd(NH_3)_4Cl_2$ and 15 g. of Amberlite 200 (a cation exchange resin from Rohm and Haas Co.).

In Examples 29 and 30, each catalyst was prepared by using 0.5 g. of rhodium trichloride trihydrate and 5 g. of Amberlyst 200.

In Example 31, the catalyst was prepared by using 0.5 g. of ruthenium trichloride monohydrate and 5 g. of Amberlite 200.

In Examples 29 and 30, the ruthenium and rhodium compounds were reduced to a zero-valent state by formalin in an aqueous solution of sodium hydroxide instead of hydrazine.

EXAMPLES 32-37

In a manner similar to that set forth in Example 6, 2 g. of benzene, 3 g. of glacial acetic acid, 0.1 g. of a hydrogenation catalyst, and 0.1 g. of a heteropolyacid catalyst were treated at 95° C., and 5 $Kg/cm^2G$ of hydrogen. The following Table shows the results obtained.

TABLE IV

| Example No. | Catalyst | Hetero-poly acid | Time (hr.) | Yield of Cyclohexane (%) | Selectivity of Cyclohexyl acetate (%) |
|---|---|---|---|---|---|
| 32 | 2% $Ru/SiO_2$ | PW-acid | 31 | 2.7 | 27.3 |
| 33 | 2% $Ru/WO_3$ | PW-acid | 31 | 7.5 | 10.7 |
| 34 | 2% $Pd/SiO_2$ | PW-acid | 15 | 15.1 | 1.4 |
| 35 | 2% $Pd/WO_3$ | PW-acid | 15 | 11.1 | 3.3 |
| 36 | 2% $Ru/WO_3$ | SW-acid | 24 | 3.5 | 17.9 |
| 37 | 2% $Pd/WO_3$ | SW-acid | 13 | 5.3 | 8.9 |

PW-acid and SW-acid represent phosphotungstic acid and silicotungstic acid, respectively. In these Examples, some cyclohexanol and phenylcyclohexane were also produced.

EXAMPLES 38-42

In a manner similar to that set forth in Example 6, formic acid and benzene were treated in the presence of a hydrogenation catalyst and an acid-acting catalyst. After a reaction time of 24 hours the analysis of the reaction mixture by means of a gas-liquid chromatograph showed that cyclohexyl formate was the sole product detected. The following Table shows the reaction conditions and the results obtained.

TABLE V

| Example No. | Reactants & Catalysts | | | $H_2$ ($Kc/Cm^2G$) | Temp. (°C.) | Yield of Cyclohexyl formate (%) |
|---|---|---|---|---|---|---|
| | Benzene (g) | HCOOH | Catalysts | | | |
| 38 | 1.0 | 1.5 | 1% $Pd/MoO_3$ PW-acid* 100 | 5 | 95 | 0.007 |
| 39 | 1.0 | 0.75 | 5% Ru/C 50 BF . 2AcOH 100 | 5 | 75 | 0.002 |
| 40 | 1.6 | 5 | 2% Rh/C 200 PW-acid 100 | 10 | 95 | 0.002 |
| 41 | 1.6 | 5 | 2% $Pt/WO_3$ 200 PW-acid 100 | 10 | 95 | 0.001 |
| 42 | 1.6 | 5 | 2% $Ir/WO_3$ 200 PW-acid 100 | 10 | 95 | 0.001 |

PW-acid represents phosphotungstic acid.
*Palladium (1% by weight) is supported on a mixture of molybdenum trioxide and phosphotungstic acid (4:1 by weight).

EXAMPLES 43-45

In a manner similar to that set forth in Example 6, 2 g. of an aromatic hydrocarbon, 4 ml. of a carboxylic acid, and 0.1 g. of 5% ruthenium-on-activated carbon catalyst were treated with 5 $Kg/cm^2G$ of hydrogen at 75° C. The following Table shows the results obtained.

TABLE VI

| Example No. | Aromatic Hydrocarbon | Carboxylic Acid | Time (hr) | Acid-acting catalyst | Conversion of aromatic hydrocarbon (%) | Selectivity of ester (%) |
|---|---|---|---|---|---|---|
| 43 | Toluene | Acetic acid | 5 | $BF_3$ . $2CH_3COOH$ 1 ml. | 6.3 | Methylcyclohexyl acetates 1.3 |
| 44 | Ethylbenzene | Acetic acid | 24 | $BF_3$ . $2CH_3COOH$ 1 ml. | 17.2 | Ethylcyclohexyl acetates 0.7 |
| 45 | Benzene | Propionic acid | 8 | Phosphotungstic acid 0.1 g. | 7.4 | Cyclohexylpropionate 0.5 |

EXAMPLES 46-49

In a manner similar to that set forth in Example 6, 1 g. of benzene, 2 ml. of 50% sulfuric acid, and 20 mg. of a hydrogenation catalyst were treated with 50 $Kg/cm^2G$ of hydrogen at 70° C. The following Table shows the results obtained.

TABLE VII

| Example No. | Hydrogenation Catalyst | Time (hr) | Yield of Cyclohexane (%) | Selectivity of cyclohexanol (%) |
|---|---|---|---|---|
| 46 | 2% $Ru/WO_3$ | 25 | 4.3 | 0.1 |
| 47 | 2% $Ru/Al_2O_3$ | 24 | 1.1 | 0.7 |
| 48 | 2% $Ru/SiO_2$ | 18 | 1.0 | 0.6 |
| 49 | 2% Ru/Zeolite | 18 | 0.8 | 0.2 |

EXAMPLES 50-54

In a manner similar to that set forth in Example 6, 1 g. of benzene, 2 ml. of 50% sulfuric acid, 20 mg. of a hydrogenation catalyst, and an appointed amount of an organic solvent were treated with 50 Kg/cm²G of hydrogen at 70° C. The following Table shows the results obtained.

TABLE VIII

| Example No. | Hydrogenation Catalyst | Organic Solvent (ml) | Time (hr) | Yield of Cyclohexane (%) | Selectivity of Cyclohexanol (%) |
|---|---|---|---|---|---|
| 50 | 2% Ru/C | CH₃COOH 0.1 | 24 | 7.3 | 0.1* |
| 51 | 2% Ru/Al₂O₃ | CH₃COOH 0.1 | 24 | 1.6 | 0.2 |
| 52 | 2% Ru/Al₂O₃ | Dioxane 0.1 | 24 | 1.1 | 0.4 |
| 53 | 2% Ru/Al₂O₃ | Dioxane 0.4 | 24 | 0.8 | 0.5 |
| 54 | 2% Ru/SiO₂ | Methanol 0.1 | 17 | 1.6 | 0.6 |

*Selectivity of cyclohexyl acetate.

EXAMPLES 55-56

In a manner similar to that set forth in Example 6, 2 ml. of benzene, 5 ml. water, 0.2 g. of 2% rhodium-on-WO₃ catalyst, and an appointed amount of phosphotungstic acid were treated with 10 Kg/cm²G of hydrogen at 95° C. for 24 hours. The following Table shows the results obtained.

TABLE IX

| Example No. | Amount of phosphotungstic acid (g) | Yield of Cyclohexane (%) | Selectivity of cyclohexanol (%) | Selectivity of cyclohexene (%) |
|---|---|---|---|---|
| 55 | 1.0 | 1.6 | 0.07 | 0 |
| 56 | 2.0 | 9.5 | 0.21 | 10.3 |

EXAMPLES 57-67

In a manner similar to that set forth in Example 6, 1 g. of benzene, 2 ml. of 50% sulfuric acid, 0.4 ml. of methanol, and 20 mg. of a hydrogenation catalyst were treated at 70° C. The following Table shows the results obtained.

TABLE X

| Example No. | Hydrogenation catalyst | Hydrogen Pressure (Kg/cm²G) | Time (hr) | Yield of cyclohexane (%) | Selectivity of cyclohexanol (%) |
|---|---|---|---|---|---|
| 57 | 2% Rh/Al₂O₃ | 5 | 6 | 32 | 0.08 |
| 58 | 2% Rh/WO₃ | 5 | 7 | 12 | 0.17 |
| 59 | 2% Rh/Zeolite | 2 | 24 | 6.9 | 0.09 |
| 60 | 2% Rh/SiO₂ | 2 | 24 | 2.5 | 1.2 |
| 61 | 2% Rh/SiO₂ | 3 | 24 | 56 | 0.98 |
| 62 | 2% Rh/SiO₂ | 10 | 6.25 | 16 | 0.19 |
| 63 | 2% Rh/SiO₂ | 20 | 2 | 23.2 | 0.03 |
| 64 | 2% Ru/SiO₂ | 5 | 24 | 0.63 | 1.75 |
| 65 | 2% Ru/SiO₂ | 10 | 6 | 1.75 | 0.46 |
| 66 | 2% Ru/SiO₂ | 20 | 24 | 8.1 | 0.26 |
| 67 | 2% Ru/SiO₂ | 40 | 24 | 20.6 | 0.14 |

EXAMPLES 68-79

In a manner similar to that set forth in Example 6, 1 g. of benzene, 2 ml. of 50% sulfuric acid, 20 mg. of a hydrogenation catalyst, and an appointed amount of a sulfate were treated with 5 Kg/cm²G of hydrogen at 70° C. The following Table shows the results obtained.

TABLE XI

| Example No. | Catalyst | Sulfate (g) | Time (hr) | Yield of cyclohexane (%) | Selectivity of cyclohexanol (%) |
|---|---|---|---|---|---|
| 68 | 2% Ru/Al₂O₃ | NaHSO₄ . H₂O (1.85) | 24 | 0.92 | 0.44 |
| 69 | 2% Ru/SiO₂ | NaHSO₄ . H₂O (0.4) | 24 | 0.56 | 1.07 |
| 70 | 2% Rh/SiO₂ | NaHSO₄ . H₂O | 7 | 16.7 | 0.19 |
| 71 | 2% Rh/SiO₂ | Ti(SO₄)₂ . 4H₂O (1) | 24 | 0.6 | 1.5 |
| 72 | 2% Rh/SiO₂ | Cr(SO₄)₃ . 9H₂O (1) | 6 | 4.8 | 0.27* |
| 73 | 2% Rh/SiO₂ | In₂(SO₄)₃ . 9H₂O (1) | 24 | 1.3 | 0.38 |
| 74 | 2% Rh/SiO₂ | Th(SO₄)₂ . 9H₂O (1) | 6.5 | 8.8 | 0.23* |
| 75 | 2% Rh/SiO₂ | Ag₂SO₄ (1) | 7.35 | 1.5 | 1.87 |
| 76 | 2% Rh/SiO₂ | BeSO₄ . 4H₂O (1) | 23 | 0.4 | 0.75 |
| 77 | 2% Rh/SiO₂ | CdSO₄ (1) | 7 | 7.5 | 0.59* |
| 78 | 2% Rh/SiO₂ | La₂(SO₄)₃ . 9H₂O (1) | 24 | 4.1 | 0.39 |
| 79 | 2% Rh/SiO₂ | UO₂SO₄ . 3H₂O (1) | 7 | 5.6 | 0.36 |

*Some amounts of cyclohexanone were also detected.

EXAMPLES 80-85

In a manner similar to that set forth in Example 6, 1 g. of benzene, 2 ml. of 50% sulfuric acid, and 0.1 g. of a hydrogenation catalyst were treated with 5 Kg/cm²G of hydrogen. The following Table shows the results obtained.

TABLE XII

| Example No. | Hydrogenation catalyst | Reaction temperature (°C.) | Reaction time (hr) | Yield of Cyclohexane (%) | Selectivity of cyclohexanol (%) |
|---|---|---|---|---|---|
| 80 | 2% Ru/SiO₂ | 60 | 24 | 2.4 | 0.75 |
| 81 | 2% Ru/SiO₂ | 100 | 24 | 1.0 | 0.68 |
| 82 | 2% Ru/SiO₂ | 100 | 24 | 15.4 | 0.19 |
| 83 | 2% Rh/SiO₂ | 60 | 16 | 45.3 | 0.03 |
| 84 | 2% Rh/SiO₂ | 80 | 7 | 29.2 | 0.05 |
| 85 | 2% Rh/SiO₂ | 100 | 7.5 | 7.1 | 0.17 |

EXAMPLES 86-92

In a manner similar to that set forth in Example 6, 2 g. of benzene, 3 ml. of glacial acetic acid, and 0.2 g. of a catalyst were treated with 5 Kg/cm²C of hydrogen at 95° C. The following Table shows the results obtained.

TABLE XIII

| Example No. | Catalyst | Time (hr) | Yield of cyclohexane | Selectivity of Cyclohexyl acetate (%) |
|---|---|---|---|---|
| 86 | 1% Pd/Neobead MSC | 15 | 17.1 | 0.02 |
| 87 | 1% Pd/Neobead P | 15 | 6.5 | 0.05 |
| 88 | 1% Pd/Silbead W | 15 | 33.4 | 0.03 |
| 89 | 1% Ru/Zeolite LaY | 30 | 2.7 | 0.17 |
| 90 | 1% Rh/Zeolite LaY | 7 | 13.1 | 0.04 |
| 91 | 1% Pd/Zeolite HY | 23 | 5.3 | 0.02 |
| 92 | 2% Pd/$TiO_2$—$Al_2O_3$ | 16 | 26.3 | 0.02 |

In Table XIII, the following notes are applicable:
In Examples 86 to 88, Neobead MSC is composed of $Al_2O_3$, Neobead P of 86% $Al_2O_3$, 9% $SiO_2$, and 3% $Na_2O$ by weight, and Silbead W of 12% $Al_2O_3$ and 88% $SiO_2$. These were obtained from Mizusawa Industrial Chemicals Ltd.

In Examples 89 to 91, Zeolite Y was obtained from Union Carbide Co.

In Example 92, a binary metal oxide, $TiO_2$-$Al_2O_3$, was prepared by a conventional co-precipitation method from a mixture of titanium chloride and aluminum nitrate in a 1:9 molar ratio.

EXAMPLE 93

A 2% ruthenium-on-phosphotungstic acid catalyst was prepared by mixing an aqueous solution of ruthenium chloride and phosphotungstic acid in an amount sufficient to provide a final catalyst containing 2% ruthenium by weight. The solution was evaporated to dryness on a water bath. The solids were dried at 110° C. for 0.5 hour and then reduced in a stream of hydrogen at 150° C. for 5 hours. The product was the desired catalyst possessing two functions of an acid-acting and hydrogenation catalyst.

In a manner similar to that set forth in Example 6, 2 g. of benzene, 3 ml. of glacial acetic acid, and 0.2 g. of the catalyst were treated with 10 Kg/cm²G of hydrogen at 110° C. for 6 hours. The analysis of the reaction mixture by means of a gas-liquid chromatograph showed that the conversion of the benzene was 11.1%, and the selectivity of cyclohexyl acetate was 12.3%.

EXAMPLES 94-102

In a manner similar to that set forth in Example 93, the preparation of catalysts and the hydrogenohydration of benzene were carried out. In each case, 3 ml. of glacial acetic acid, 2 g. of benzene, and 0.2 g. of a catalyst were treated under a hydrogen pressure of 10 Kg/cmG². The following Table shows the results obtained.

In the Table, PW and SiW represent phosphotungstic acid and silicotungstic acid, respectively.

TABLE XIV

| Example No. | Catalyst | Temp. (°C.) | Time (hr) | Yield of Cyclohexane (%) | Selectivity of cyclohexyl acetate (%) |
|---|---|---|---|---|---|
| 94 | 1% Ru/PW | 130 | 6 | 3.5 | 13.7 |
| 95 | 1% Ru/PW | 125 | 1 | 8.9 | 7.4 |
| 96 | 2% Ru/PW | 110 | | 2.3 | 21.0 |
| 97 | 2% Ru/SiW | 110 | 6 | 1.3 | 19.4 |
| 98 | 0.1% Rh/PW | 110 | 23 | 5.3 | 6.8 |
| 99 | 0.1% Pd/PW | 110 | 7 | 3.9 | 6.9 |
| 100 | Ru/PW/$MoO_3$ | 110 | 22 | 0.5 | 29.6 |
| 101 | Ru/PW/$WO_3$ | 95 | 21 | 0.9 | 20.8 |
| 102 | Ru/PW/$SiO_2$ | 110 | 21 | 0.2 | 33.0 |

In Example 95, the amount of the catalyst was 50 mg. and the pressure of hydrogen was 60 Kg/cm²G.

In Examples 100, 101 and 102, the catalysts comprise 0.5% of ruthenium and a support of a mixture of phosphotungstic acid and a metal oxide (1:1 by weight).

EXAMPLES 103-110

In a manner similar to that set forth in Example 6, 1 g. of benzene, 2 ml. of glacial acetic acid, 0.2 g. of a hydrogenation catalyst, and an acid catalyst were treated with 10 Kg/cm²G of hydrogen at 110° C. Each hydrogenation catalyst was prepared in a manner similar to that set forth in Example 93 by mixing two kinds of noble metal halides and silica gel in water in an amount sufficient to provide a final catalyst containing 5% noble metals in a mixture of an appointed weight ratio in Table XV. The following Table shows the results obtained.

TABLE XV

| Example No. | Hydrogenation catalyst (ratio) | Acid catalyst (g.) | Time (hr) | Yield of Cyclohexane (%) | Selectivity of cyclohexyl acetate (%) |
|---|---|---|---|---|---|
| 103 | Ru—Pd (2:8) | P W (0.2) | 0.35 | 10.2 | 2.7 |
| 104 | Ru—Pt (8:2) | P W (0.2) | 0.25 | 11.4 | 1.1 |
| 105 | Ru—Ir (2:8) | P W (0.2) | 0.18 | 13.6 | 0.1 |
| 106 | Os—Pt (2:8) | P W (0.2) | 0.10 | 8.6 | 1.1 |
| 107 | Pd—Pt (2:8) | P W (0.2) | 0.15 | 9.5 | 0.8 |
| 108 | Os—Pd (8:2) | P W (0.2) | 0.33 | 8.2 | 3.6 |
| 109 | Rh—Ru (6:4) | $BF_3$—2AcOH (1.0) | 0.37 | 12.6 | 1.5 |
| 110 | Rh—Ru (6:4) | Si W (0.2) | 0.22 | 7.4 | 4.6 |

EXAMPLES 111-114

In a manner similar to that set forth in Example 6, 2 g. of benzene, 2 ml. of acetic acid, 0.2 g. of a hydrogenation catalyst, and an aqueous acid were treated with 10 Kg/cm²G of hydrogen. Each hydrogenation catalyst comprises a noble metal (5 weight percentage) and a silica gel support.

TABLE XVI

| Example No. | Hydrogenation Catalyst | Acid catalyst | Time (Hr) | Yield of cyclohexane (%) | Selectivity of cyclohexyl acetate (%) |
|---|---|---|---|---|---|
| 111 | Ru | 30% $H_2SO_4$ 2 ml. | 17 | 14.4 | 1.5 |

TABLE XVI-continued

| Example No. | Hydrogenation Catalyst | Acid catalyst | Time (Hr) | Yield of cyclohexane (%) | Selectivity of cyclohexyl acetate (%) |
|---|---|---|---|---|---|
| 112 | Ru | 0.4g PW, 2 ml. $H_2O$ | 17 | 22.8 | 0.1 |
| 113 | Ru—Rh (2:8) | 24.3% HCl 5 ml. | 7.33 | 6.4 | 4.4 |
| 114 | Os—Pd (8:2) | 24.3% HCl 5 ml. | 7.33 | 4.8 | 2.2 |

EXAMPLE 115

In a manner similar to that set forth in Example 93, 1 ml. of benzene, 2 ml. of 40% sulfuric acid, 0.1 g. of the hydrogenation catalyst described in Example 93 were treated with 5 Kg/cm$^2$G of hydrogen at 100° C., for 20 hours. The analysis of the reaction mixture by means of a gas-liquid chromatograph showed that the conversion of the benzene was 1.8%, and the selectivity of cyclohexanol was 0.52%.

EXAMPLE 116

A mixture of 10 g. of 20% colloidal silica ("Snowtex-N", Nissan Chemical Industries, Ltd.), 0.23 ml. of 10% aqueous ruthenium chloride (RuCl$_3$.H$_2$O), and 1.49 ml. of 10% aqueous silver nitrate (AgNO$_3$) was dried in vacuo at 60°-80° C. The residue was ground finely enough to pass through a 100 mesh sieve, reduced with hydrogen under atmospheric pressure at 150° C. for 5 hours, allowed to stand overnight in an atmosphere of ammonia at room temperature, washed with distilled water, and finally dried with hydrogen under atmospheric pressure at 150° C., for 5 hours. The catalyst thus obtained is expressed as 5%Ru-Ag(1:9)/SiO$_2$.

In a high pressure glass bomb (ca. 20 ml), 200 mg. of the catalyst prepared above, 2 ml. of benzene, and 5 ml. of 40% sulfuric acid were provided with a small bar magnet coated with polytetrafluoroethylene. After replacement with hydrogen, the bomb was heated at 100° C. under 10 Kg/cm$^2$G pressure of hydrogen for 4 hours with magnetic stirring. After neutralization with about 13 ml. of aqueous alkali (ca. 40%K$_3$PO$_4$-NaOH), the product was submitted to gas-liquid chromatography (column: 25%PEG-4000/C-22, 60–80 mesh, 3 m., 150° C., H$_2$ 20 ml./min). The chromatogram showed that the conversion of benzene was 1.39%, and the yields of cyclohexanol, cyclohexane, and cyclohexene were 0.42%, 0.77%, and 0.20%, respectively. The selectivity of cyclohexanol was 30%.

EXAMPLES 117–130

These experiments were carried out in a manner similar to that described in Example 116, and the resulting data are summarized in Table XVII.

TABLE XVII

| Example No. | Catalyst | Conditions | Cyclohexanol (Selectivity) | Cyclohexane | Cyclohexene |
|---|---|---|---|---|---|
| 117 | 5% Ru—Cu(3:7)/SiO$_2$ | A | 0.15 (44) | 0.16 | 0.04 |
| 118 | 5% Ru—Ag(9:1)/SiO$_2$ | A | 0.10 (3.9) | 2.4 | 0.12 |
| 119 | 0.7% Ru/Ag | A | 0.01 (5.0) | 0.21 | 0.004 |
| 120 | 5% Ru/Cu(99:1)/SiO$_2$ | A | 0.09 (4.0) | 2.1 | 0.009 |
| 121 | 5% Ru—Cu(5:5)/SiO$_2$ | A | 0.21 (15) | 1.1 | 0.09 |
| 122 | 5% Ru—Ag(3:7)/SiO$_2$ | A | 0.30 (12) | 2.0 | 0.23 |
| 123 | 2% Ru—Ag(2:8)SrSO$_4$—SiO$_2$ (3:7) | A | 0.018 (6.6) | 0.22 | 0.034 |
| 124 | 5% Ru—Ag(5:95)/SiO$_2$* | A | 0.12 (32) | 0.19 | 0.07 |
| 125 | 20% Ru—(3:7)/SiO$_2$ | A | 0.16 (13) | 0.98 | 0.11 |
| 126 | 5% Rh—Ag(7:3)/SiO$_2$ | A | 0.12 (3.3) | 3.2 | 0.29 |
| 127 | 5% Rh—Ag(2:8)/SiO$_2$ | B | 0.39 (5.7) | 5.7 | 0.86 |
| 128 | 5% Rh—Cu(2:8)/SiO$_2$ | B | 0.13 (14) | 0.67 | 0.10 |
| 129 | 2% Ru—Ag(2:8)/CaSo$_4$—SiO$_2$ (3:7) | A | 0.29 (24) | 0.79 | 0.14 |
| 130 | 5% Ru—Ag(2:8)/SiO$_2$ | C | 0.12 (21) | 0.41 | 0.013 |

Reaction Conditions
A : catalyst 200 mg, benzene 2 ml., 40% H$_2$SO$_4$ 5 ml., H$_2$ 10Kg/cm$^2$G, 100° C., 4 hrs.
B : catalyst 100 mg, the others are the same as above.
C : catlyst 200 mg, benzene 2 ml., 55% H$_2$SO$_4$ 5 ml., H$_2$ 10 Kg/cm$^2$G, 60° C., 7 hrs.

*The catalyst was prepared from 5% Ag/SiO$_2$ and 10% aq. Ru(NO$_3$)$_3$ by means of exchange of metal cations.

EXAMPLES 131–141

The following experiments were carried out in a manner similar to that described in Example 116, and the data obtained are tabulated in Table XVIII.

TABLE XVIII

| Ex. No. | Catalyst | Cyclohexanol (selectivity) | Cyclohexane | Cyclohexene |
|---|---|---|---|---|
| 131 | 5% Ru—Ag(15:85)/SiO$_2$ | 0.15 (4.6) | 2.6 | 0.56 |
| 132 | 5% Ru—Cu(4:6)/SiO$_2$ | 0.10 (6.8) | 1.2 | 0.25 |
| 133 | 5% Ru—Cu—Ag(4:3:3)/SiO$_2$ | 0.062 (12) | 0.26 | 0.21 |
| 134 | 5% Ru—Cu—Ag(6:2:2)/SiO$_2$ | 0.39 (6.4) | 4.8 | 0.91 |
| 135 | 5% Rh—Ag(2:8)/SiO$_2$ | 0.30 (1.4) | 18.5 | 2.0 |
| 136 | 5% Rh—Cu(2:8)/SiO$_2$ | 0.07 (5.4) | 0.97 | 0.17 |
| 137 | 5% Pd—Ag(7:3)/SiO$_2$ | 0.004 (0.1) | 3.8 | 0.05 |
| 138 | 5% Pd—Cu(9:1)/SiO$_2$ | 0.005 (0.36) | 1.3 | 0.03 |
| 139 | 5% Ir—Ag(7:3)/SiO$_2$ | 0.009 (0.96) | 0.83 | 0.02 |

TABLE XVIII-continued

| Ex. No. | Catalyst | Yields of Products (%) | | |
|---|---|---|---|---|
| | | Cyclohexanol (selectivity) | Cyclo-hexane | Cyclo-hexene |
| 140 | 5% Pt—Ag(9:1)/SiO$_2$ | 0.014 (0.08) | 18.4 | 0.14 |
| 141 | 5% Pt—Cu(9:1)/SiO$_2$ | 0.011 (0.09) | 12.9 | 0.01 |

Reaction conditions: Catalyst 50 mg, benzene 2 ml, 40% H$_2$SO$_4$ 5 ml, H$_2$ 10 Kg/cm$^2$G, 100° C., 20 hrs.

EXAMPLES 142–145

In the following Examples, experiments were carried out in a manner similar to that described in Example 116, by the use of 5 ml. of an aqueous mixture of sulfuric acid (26%) and acetic acid (29%) instead of 5 ml. of 40% sulfuric acid as in Example 116. The results obtained are summarized in Table XIX.

TABLE XIX

| Example No. | Catalyst (amount) | Conversion of benzene (%) | Selectivities of Products (%) | | |
|---|---|---|---|---|---|
| | | | Cyclohexyl-acetate | Cyclo-hexanol | Cyclo-hexene |
| 142 | 5% Ru—Ag(2:8)/SiO$_2$ (100 mg) | 14.9 | 15.4 | 1.5 | 5.9 |
| 143 | 5% Ru—Cu(4:6)/SiO$_2$ (100 mg) | 2.6 | 27.6 | 2.8 | 9.9 |
| 144 | 5% Rh—Ag(4:6)/SiO$_2$ (100 mg) | 40.9 | 9.4 | 0.7 | 2.4 |
| 145 | 5% Rh—Cu(7:3)/SiO$_2$ (200 mg) | 19.9 | 14.5 | 1.5 | 6.1 |

Reaction conditions: Benzene 2 ml, 26%H$_2$SO$_4$-29%AcOH 5 ml, H$_2$ 10 Kg/cm$^2$G, 100° C., 20 hrs.

EXAMPLES 146–159

In the following Examples, the designated amount of catalyst, 2 ml. of benzene, and 5 ml. of an aqueous solution of sulfuric acid (20%) and acetic acid (45%) were used in a manner similar to that in Example 116, under similar conditions (H$_2$ 10 Kg/cm$^2$G, 100° C., 4 hrs). The data are summarized in Table XX.

TABLE XX

| Example No. | Catalyst (amount) | Conversion of benzene (%) | Selectivity of Products (%) | | |
|---|---|---|---|---|---|
| | | | Cyclohexyl-acetate | Cyclo-hexanol | Cyclo-hexene |
| 146 | 5% Ru—Ag(7:3)/SiO$_2$ (50 mg) | 16.0 | 7.2 | 1.1 | 11.6 |
| 147 | 5% Ru—Ag(15:85)/SiO$_2$ (20 mg) | 0.41 | 42.8 | 3.6 | 7.5 |
| 148 | 5% Ru—Cu(3:7)/SiO$_2$ (20 mg) | 0.17 | 44.2 | 3.6 | 10.9 |
| 149 | 5% Ru—Ag(7:3)/SiO$_2$ (50 mg) | 7.8 | 5.3 | 0.8 | 7.7 |
| 150 | 5% Ru—Ag(1:9)/SiO$_2$ (50 mg) | 0.68 | 17.7 | 2.5 | 29.3 |
| 151 | 5% Ru—Cu(4:6)/SiO$_2$ (50 mg) | 0.83 | 10.2 | 2.3 | 13.5 |
| 152 | 5% Rh—Cu(7:3)/SiO$_2$ (50 mg) | 1.7 | 5.9 | 1.1 | 7.4 |
| 153 | 5% Pd—Ag(7:3)/SiO$_2$ (50 mg) | 1.7 | 4.2 | 0.7 | 4.6 |
| 154 | 5% Pd—Cu(9:1)/SiO$_2$ (50 mg) | 1.2 | 2.1 | 0.3 | 1.9 |
| 155 | 5% Ir—Ag(9:1)/SiO$_2$ (50 mg) | 13.2 | 0.8 | 0.1 | 0.9 |
| 156 | 5% Pt—Ag(9:1)/SiO$_2$ (50 mg) | 12.8 | 0.8 | 0.1 | 1.0 |
| 157 | 5% Pt—Cu(9:1)/SiO$_2$ (50 mg) | 9.4 | 0.6 | 0.1 | 0.7 |
| 158 | 5% Ru—Ag—Cu(4:3:3)/SiO$_2$ (50 mg) | 0.24 | 16.1 | 1.7 | 26.3 |
| 159 | 5% Ru—Ag—Cu(6:2:2)SiO$_2$ (50 mg) | 2.8 | 9.7 | 1.6 | 15.4 |

EXAMPLE 160

A catalyst of ruthenium and silver supported on La$^{+3}$Y zeolite was obtained as follows: The La$^{+3}$ exchanged zeolite Y was prepared by repeatedly immersing SK-40 powder of the Linde Co. in 1 N aqueous solution of lanthanum trichloride, and then drying at 110° C. after washing with distilled water. To a rapidly agitated slurry of 40 g. of the La$^{+3}$ exchanged zeolite in 120 ml. water, was added a solution of 1.824 g. of ruthenium trichloride monohydrate in 400 ml. water during a period of 3 hrs. The slurry was stirred for 15 hrs. and then filtered. The resulting solid was washed with distilled water and dried in vacuo at 110° C. for 5 hrs. The product corresponds to a LaY zeolite containing 2 percent of ruthenium(+3). In a manner similar to the Ru$^{+3}$-loading procedure set forth above, Ag$^{+1}$ was loaded by mixing an aqueous slurry of 10 g. of the 2%Ru-LaY zeolite and an aqueous solution of 0.785 g. of silver nitrate, and then drying in vacuo at 110° C. after washing with distilled water. The material was slowly heated in a stream of nitrogen from room temperature to 550° C. in 2 hrs. It was then held at 550° C. for 3 hrs. The product was the desired catalyst designed for providing a final catalyst containing 7% (wt.)Ru-Ag(2:5) on LaY zeolite.

Into a glass vessel (ca. 35 ml) (having a coiled capillary vent together with a small bar magnet coated with polytetrafluoroethylene) were placed 4 g. of benzene, 6 ml. of glacial acetic acid and 0.2 g. of the 7%Ru-Ag(2:5)-on-LaY catalyst. The vessel was placed in an autoclave (ca. 100 ml) of Hastelloy B. After the autoclave was flushed with hydrogen, it was heated by placing it in an oil bath warmed at 180° C., and pressured with 20 Kg/cm$^2$G of hydrogen. The bar magnet was set into motion by an external magnetic stirrer for 2 hrs. Then the autoclave was chilled in an ice-water bath. The reaction mixture was treated in a manner similar to that set forth in Example 1, and subjected to analysis by means of a gas-liquid chromatograph. This analysis showed that the conversion of benzene was 4.4%, and the selectivities of cyclohexyl acetate and cyclohexene were 12% and 8%, respectively.

EXAMPLES 161–164

The preparation of catalysts and the hydrogenohydration of benzene were carried out under conditions similar to those set forth in Example 160. The following Table shows the results obtained.

TABLE XXI

| Example No. | Catalyst | $H_2$ (Kg/cm²G) | Yield of Cyclohexane | Selectivity (%) Cyclohexyl acetate | Cyclohexene |
|---|---|---|---|---|---|
| 161 | 3% Ru—Ag(2:1)Lay | 20 | 6.9 | 9.2 | 8.2 |
| 162 | 2% Ru/CuY | 50 | 4.2 | 3.4 | 18.9 |
| 163 | 2% Ru/AgY | 20 | 1.6 | 0.4 | 32.4 |
| 164 | 2% Ru(1:3)/LaY | 20 | 3.5 | 4.0 | 18.3 |

EXAMPLES 165–172

In these Examples, 50 mg. of a catalyst whose composition was 5%Ru-Ag-Cu(5:4:1)/SiO₂, 2 ml. of benzene, 5 ml. of 40% sulfuric acid, and 1 ml. of an alcohol listed in Table XXII were used as starting materials in a similar manner to that described in Example 116 under similar conditions (H₂ 10 Kg/cm²G, 100° C., 20 hrs.) The results are tabulated in Table XXII.

TABLE XXII

| Example No. | Alcohol | Yields of Products (%) Cyclohexane | Cyclohexene | Cyclohexanol | Selectivity of cyclohexanol (%) |
|---|---|---|---|---|---|
| 165 | n-Propanol | 14.4 | 3.5 | 1.5 | 8. |
| 166 | n-Butanol | 13.1 | 4.1 | 2.7 | 13. |
| 167 | Isobutanol | 7.4 | 2.3 | 1.9 | 16. |
| 168 | n-Amyl alcohol | 10.2 | 3.7 | 2.5 | 15. |
| 169 | n-Hexanol | 11.1 | 4.7 | 2.8 | 15. |
| 170 | n-Octanol | 10.2 | 2.5 | 1.6 | 16. |
| 171 | 1,4-butanediol* | 3.4 | 1.1 | 0.7 | 14. |
| 172 | 1,6-hexanediol* | 1.1 | 0.3 | 0.2 | 11. |

*In these cases, 0.25 ml. of an alcohol was used.

EXAMPLES 173–177

In the following Examples, a catalyst listed in Table XXIII, was used with 2 ml. of benzene, 5 ml. of 40% sulfuric acid, and 1 ml. of n-butanol in a manner similar to that of the above Examples, under similar conditions (10 Kg/cm²G pressure of hydrogen, 100° C., 20 hrs.)

TABLE XXIII

| Example No. | Catalyst (amount) | Yields of Products (%) Cyclohexane | Cyclohexene | Cyclohexanol | Selectivity of Cyclohexanol (%) |
|---|---|---|---|---|---|
| 173 | 5% Ru—Cu(7:3)/SiO₂ (200 mg) | 19.2 | 2.9 | 2.0 | 8.3 |
| 174 | 5% Ru—Cu(3:7)/SiO₂ (200 mg) | 1.0 | 0.8 | 0.6 | 25. |
| 175 | 5% Rh—Ag—Cu(4:3:3) SiO₂ (50 mg) | 3.6 | 0.4 | 0.4 | 8. |
| 176 | 5% Ru—Ag—Cu(6:2:2)SiO₂ (50 mg) | 19.0 | 1.7 | 1.2 | 5.3 |
| 177* | 5% Ru—Ag—Cu(6:3:1)SiO₂ (50 mg) | 13.8 | 3.6 | 2.6 | 13. |

*In this case, reaction was carried out for 16 hours.

EXAMPLES 178–181

In these Examples, 50 mg. of a catalyst listed in Table XXIV, was used with 2 ml. of benzene and 5 ml. of 40% sulfuric acid in a manner similar to that described in Example 116, under similar conditions (10 Kg/cm²G pressure of hydrogen, 100° C., and 20 hours). The following Table shows the results obtained.

TABLE XXIV

| Example No. | Catalyst | Yields of Products (%) Cyclohexane | Cyclohexene | Cyclohexanol | Selectivity of Cyclohexanol (%) |
|---|---|---|---|---|---|
| 178 | 5% Ru—Re—Cu(6:1:3)/SiO₂ | 4.5 | 0.9 | 0.4 | 7 |
| 179 | 5% Rh—Re—Ag(6:1:3)/SiO₂ | 26.1 | 0.8 | 0.5 | 2 |
| 180* | 5% Ru—Re—Ag(6:2:2)/SiO₂ | 19.0 | 1.7 | 1.2 | 5 |
| 181** | 5% Ru—Re—Ag(6:1:3)/SiO₂ | 1.7 | 0.1 | 0.2 | 11 |

*In this case, 1 ml. of n-butanol was added to the starting materials.
**In this case, reaction was carried out for 4 hours.

EXAMPLES 182–187

The following Examples were carried out using 200 mg. of a catalyst indicated in Table XXV, with 2 ml. of benzene and 5 ml. of an aqueous mixture of sulfuric acid (20%) and acetic acid (45%), in a manner similar to that described in Example 116, under similar conditions (10 Kg/cm²G pressure of hydrogen, 100° C., and 4 hours).

TABLE XXV

| Example No. | Catalyst | Conversion of benzene (%) | Yields of Products (%) Cyclohexyl acetate | Cyclohexanol | Cyclohexene |
|---|---|---|---|---|---|
| 182 | 5% Ru—Re—Ag(6:1:3)/SiO₂ | 4.7 | 0.5 | 0.1 | 1.0 |
| 183 | 5% Ru—Re—Cu(6:2:2)/SiO₂ | 3.8 | 0.4 | 0.1 | 0.5 |
| 184 | 5% Rh—Re—Ag(6:1:3)/SiO₂ | 20. | 1.0 | 0.3 | 1.6 |

TABLE XXV-continued

| Example No. | Catalyst | Conversion of benzene (%) | Yields of Products (%) | | |
|---|---|---|---|---|---|
| | | | Cyclohexyl acetate | Cyclohexanol | Cyclohexene |
| 185 | 5% Rh—Re—Cu(6:3:1)/SiO$_2$ | 22. | 0.7 | 0.2 | 1.1 |
| 186 | 5% Ru—Re—Ag·Cu/SiO$_2$ | 1.9 | 0.2 | 0.1 | 0.4 |
| 187 | 5% Rh—Re—Ag—Cu/SiO$_2$ (5:2:2:1) | 6.1 | 0.3 | 0.1 | 0.4 |

EXAMPLES 188–192

The following Examples, summarized in Table XXVI, were carried out using 50 mg. of a catalyst listed in the Table with 2 ml. of benzene and 5 ml. of an aqueous solution of sulfuric acid (40%) and acetic acid (2%), in a manner similar to that described in Example 116, under similar conditions (10 Kg/cm$^2$G pressure of hydrogen, 100° C., and 4 hours).

TABLE XXVI

| Example No. | Catalyst | Yields of Products (%) | | | | Selectivity of Cyclohexanol (%) |
|---|---|---|---|---|---|---|
| | | Cyclohexane | Cyclohexene | Cyclohexylacetate | Cyclohexanol | |
| 188 | 2% Ru/ZrO$_2$—SiO$_2$ (3:7) | 0.57 | 0.01 | 0.01 | 0.04 | 6.3 |
| 189 | 2% Ru/Ta$_2$O$_5$—SiO$_2$ (3:7) | 1.3 | 0.04 | 0.12 | 0.12 | 7.7 |
| 190 | 2% Rh/Nb$_2$O$_5$—SiO$_2$ (3:7) | 3.1 | 0.03 | 0.004 | 0.03 | 0.9 |
| 191 | 2% Rh/Ta$_2$O$_5$—SiO$_2$ (3:7) | 3.7 | 0.04 | 0.01 | 0.05 | 1.3 |
| 192 | 2% Rh/WO$_3$—SiO$_2$ (3:7) | 3.4 | 0.05 | 0.01 | 0.05 | 1.5 |

We claim:
1. A process for producing a cyclohexane derivative having the general formula

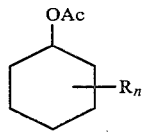

wherein Ac is selected from the group consisting of hydrogen, formyl, acetyl and propionyl groups, R is a lower alkyl group having 1 to 3 carbon atoms, and n is an integer of from 0 to 2, which process comprises reacting an aromatic hydrocarbon having the general formula

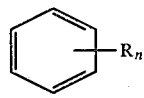

wherein R and n are the same as above, with hydrogen and a compound having the general formula HOAc wherein Ac is the same as above, in the presence of a strong acid and a hydrogenatin catalyst comprising a combination of at least two noble metals selected from the group consisting of Ru, Rh, Pd, Os, Ir, and Pt.

2. The process of claim 1, wherein the strong acid is an organosulfonic acid.

3. The process of claim 2, wherein the organosulfonic acid is selected from the group consisting of trifluoromethanesulfonic acid, methanesulfonic acid, benzenesulfonic acid, and toluenesulfonic acid.

4. The process of claim 1, wherein the strong acid is a heteropolyacid.

5. The process of claim 4, wherein the heteropolyacid is selected from the group consisting of phosphomolybdic acid, phosphotungstic acid, silicomolybdic acid, and silicotungstic acid.

6. The process of claim 1, wherein the strong acid is sulfuric acid.

7. The process of claim 1, wherein the strong acid is boron trifluoride.

8. The process of claim 1, wherein the strong acid is an ion-exchange resin having strongly acidic functional groups selected from the group consisting of sulfonic acid, phenylsulfonic acid and phosphonic acid.

9. The process of claim 1, wherein the hydrogenation catalyst contains a combination of noble metals selected from the group consisting of ruthenium-rhodium, rhodium-palladium, palladium-osmium and rhodium-ruthenium-platinum.

10. The process of claim 1, wherein the hydrogenation catalyst further contains at least one metal selected from the group consisting of copper, silver, gold and rhenium.

11. The process of claim 1, wherein a carrier is employed in addition to the hydrogenation catalyst.

12. The process of claim 11, wherein the carrier is selected from the group consisting of active carbon, silica, alumina, silica-alumina, boria, tungsten trioxide, molybdenum trioxide, zeolites, asbestos, solid acids, and cation-exchange resins.

13. The process of claim 1, wherein the Ac group is an acetyl group.

14. The process of claim 1, wherein the reaction temperature is in the range of 0° to 300° C.

15. The process of claim 1, wherein the pressure of hydrogen is in the range of 0.01 to 500 Kg/cm$^2$G.

16. The process of claim 1, wherein the conversion of the aromatic hydrocarbon is less than 80 percent.

17. The process of claim 1, wherein the strong acid has an acid dissociation constant pKa of less than 2.0.

* * * * *

UNITED STATES PATENT AND TRADEMARK OFFICE
CERTIFICATE OF CORRECTION

PATENT NO. : 4,212,990
DATED : July 15, 1980
INVENTOR(S) : Yutaka Yasuhara et al It is certified that error appears in the above-identified patent and that said Letters Patent are hereby corrected as shown below:

In column 8, Table V, Example No. 39, please insert the following: After "BF" insert below the line --3--

In column 19, Table XXV, Example No. 186, please insert the following: After "5% Ru-Re-Ag-Cu/SiO$_2$" --(5:2:2:1)--

Signed and Sealed this

Eleventh Day of November 1980

[SEAL]

Attest:

SIDNEY A. DIAMOND

Attesting Officer

Commissioner of Patents and Trademarks